United States Patent [19]
Francis et al.

[11] Patent Number: 5,569,163
[45] Date of Patent: Oct. 29, 1996

[54] DISPOSABLE SURGICAL INSTRUMENT

[75] Inventors: William J. Francis, Quincy, Mass.; Paul A. Scirica, Huntington, Conn.

[73] Assignee: United States Surgical Corporation, Norwalk, Conn.

[21] Appl. No.: 306,094

[22] Filed: Sep. 14, 1994

[51] Int. Cl.$^6$ ........................................................ A61B 1/04
[52] U.S. Cl. ............................ 600/133; 600/162; 359/510
[58] Field of Search ................................... 606/182, 219, 606/15, 16, 17; 600/133, 162; 607/90, 93; 359/510, 511

[56] References Cited

U.S. PATENT DOCUMENTS

| | | |
|---|---|---|
| 4,955,959 | 9/1990 | Tompkins et al. . |
| 4,964,710 | 10/1990 | Leiner . |
| 5,281,214 | 1/1994 | Wilkins et al. ........................ 606/15 |
| 5,313,935 | 5/1994 | Kortenbach et al. . |
| 5,342,396 | 8/1994 | Cook ........................................ 606/219 |

FOREIGN PATENT DOCUMENTS 0581400  2/1994  European Pat. Off. .

OTHER PUBLICATIONS

POLYOX® Water–Soluble Resins Booklet, Union Carbide Chemicals and Plastics Company, Inc., 1988.

*Primary Examiner*—Richard J. Apley
*Assistant Examiner*—Beverly M. Flanagan

[57] ABSTRACT

A surgical instrument includes at least one member fabricated with a material which is capable of deforming in the presence of a deforming agent such as water, organic solvent, air, heat, light, etc. Thus, a disposable surgical endoscope is provided wherein a lens mounting element for aligning a lens assembly of the endoscope with the other optical components of the instrument is fabricated from a polymer which deforms when exposed to, e.g., water or organic solvents. Deformation of the lens mounting element causes the lens assembly to shift out of optical alignment with the other optical components of the device, thereby disabling the instrument.

20 Claims, 4 Drawing Sheets

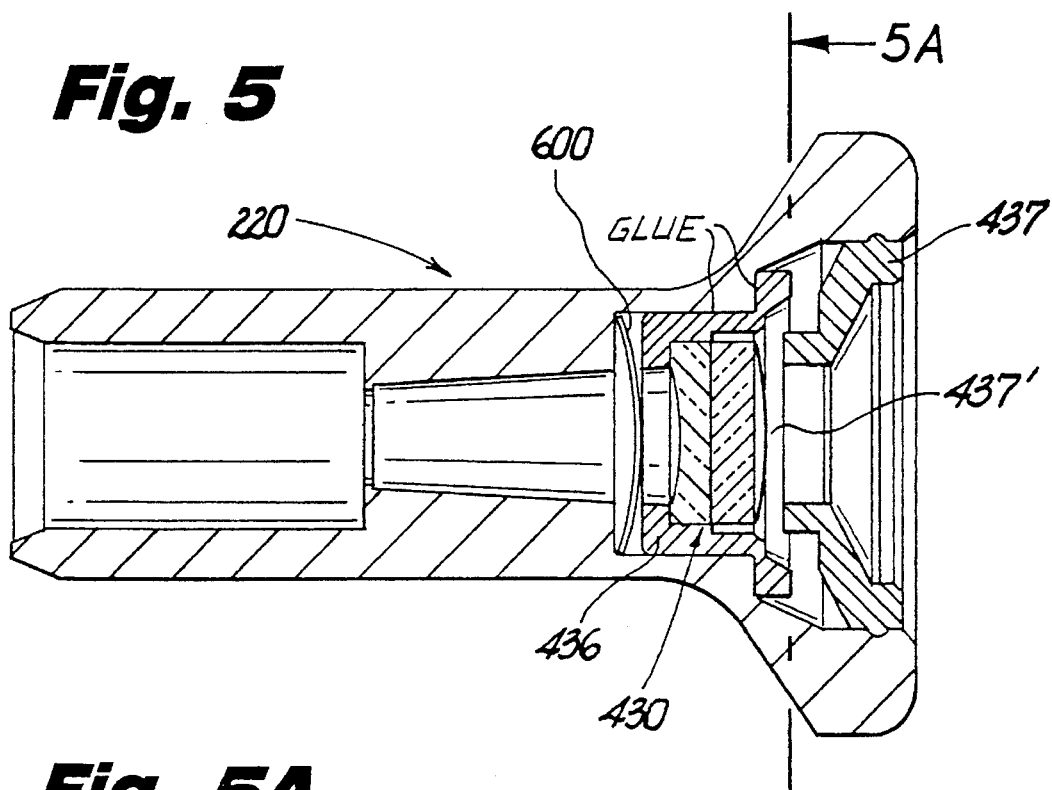
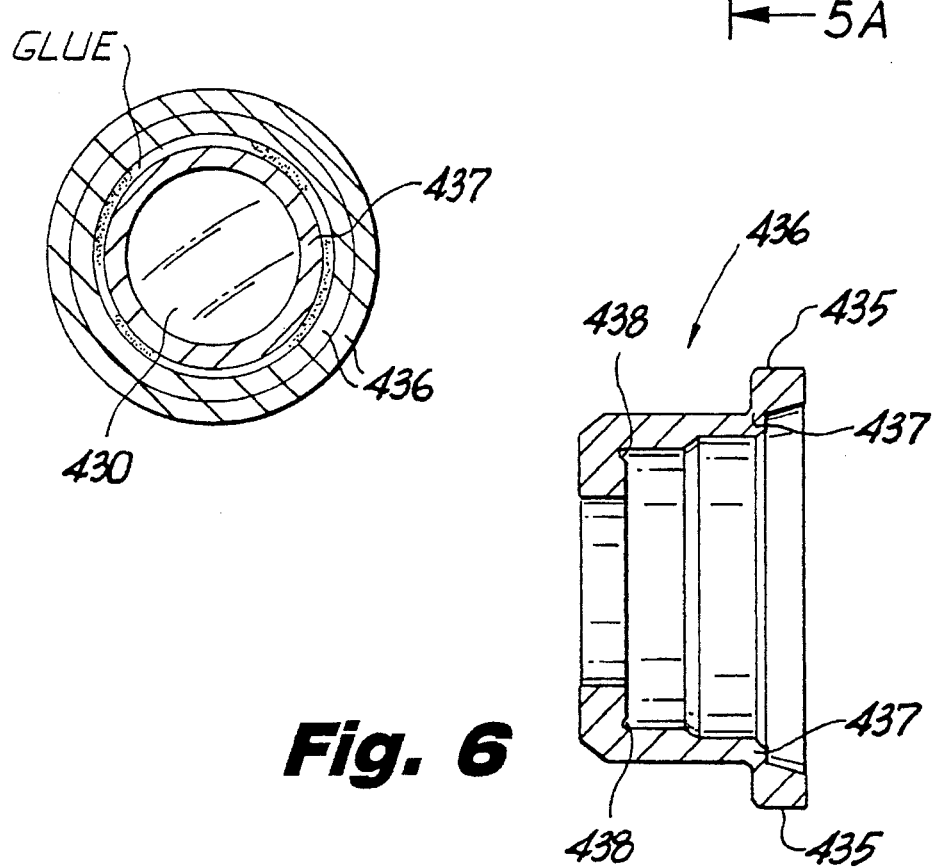

5,569,163

DISPOSABLE SURGICAL INSTRUMENT

BACKGROUND OF THE INVENTION

1. Technical Field

The present disclosure generally relates to a disposable surgical instrument and, more particularly, to a surgical instrument which can be utilized a limited number of times before being rendered inoperable by the occurrence of at least one instrument-disabling phenomenon.

2. Background of Related Art

Increasingly, surgeons are employing disposable surgical instruments which are designed to be used a limited number of times and thereafter discarded. Many disposable instruments are intended to be employed once in a single surgical operation. Disposable surgical instruments possess a number of advantages over reusable surgical devices, e.g., they can be fabricated from less expensive materials compared to reusable devices and consequently reduce the overall cost of surgery, they perform optimally since they are not subject to the wear and tear of repeated use, and they minimize the risk that infectious diseases will be transmitted to other patients.

It is important, however, to recognize that disposable surgical instruments are often equipped for use in a single procedure, e.g., by reason of a limited number of staples or clips, and are generally not designed to withstand many repeated resterilizations and reuses. For example, surgical staplers, clip appliers, and the like, have been provided with lock-out mechanisms which preclude actuation of the devices after they have been actuated a predetermined number of times. See, e.g., U.S. Pat. No. 4,955,959. Surgical devices which include mechanisms for displaying the number of times the device has been used (U.S. Pat. No. 5,313,935) or the number of times the device has been heated, e.g., by autoclave sterilization (EP0581400), are known.

An endoscope, i.e., an instrument used in surgery to view internal portions of a patient's body, is a long, slender instrument having a shaft which is either rigid or flexible, depending on the procedure being performed, and an optical lens system for focusing on and relaying an illuminated image from inside a body cavity to a physician. Essential optical components of a conventional optical system include a combination of lenses constituting an objective lens for forming a focused real image of an object, a system of relay lenses to carry the image through the endoscope, and an eye lens assembly which produces a magnified virtual image for the viewer. In general, the objective lens is positioned adjacent a distal end and the eye lens assembly is mounted at the proximal end of the endoscope. Endoscopes are commonly equipped with an illumination system, e.g., a fiber optic bundle, which illuminates the area being imaged. Generally, a camera adaptor is provided at the proximal end of the endoscope to permit the image to be displayed on a monitor for viewing by the entire surgical team.

It has been found necessary and advantageous, therefore, to furnish disposable surgical instruments with at least one disabling means which, after being initiated, exerts a disabling effect on the instrument and thereby permanently or temporarily precludes further use of the instrument. It has also been found expedient to furnish a disposable endoscope with disabling means to prevent the endoscope from being used beyond a predetermined number of times.

SUMMARY

In accordance with the present disclosure, a disposable surgical instrument, e.g., a disposable endoscope, is provided wherein at least one member of the instrument deforms in the presence of a deforming agent, thereby disabling the instrument from further use. To carry out this objective, the member is fabricated from a material, e.g., a polymer, which is capable of undergoing a relatively rapid structural deformation when exposed to one or more phenomena such as heat, water, light, organic solvents, certain gases, or the like. For example, the member can be fabricated from a water-soluble polymer. Deformation of the member results when an attempt to wash and/or resterilize the instrument is made after the instrument has been removed from its package. Upon contact with water, the member fabricated from the water-soluble polymer structurally weakens or deforms, i.e., becomes rubbery and/or partially or completely dissolves. As a result of the deformation of the member fabricated with the water-soluble polymer, the instrument is disabled from further use.

BRIEF DESCRIPTION OF THE DRAWINGS

Various embodiments are described herein with reference to the drawings, wherein:

FIG. 5 is an enlarged cross-sectional view of another embodiment of the proximal end of the disposable endoscope disclosed herein;

FIG. 5A is a cross-sectional view taken along line 5A—5A of FIG. 5;

FIG. 6 is an enlarged cross-sectional view of the lens mounting element depicted in FIG. 5.

DETAILED DESCRIPTION OF PREFERRED EMBODIMENTS

While the principles of the present disclosure are disclosed herein in connection with particular disposable surgical instruments, it shall be understood that these principles are broadly applicable to a wide array of disposable surgical devices. Thus, e.g., trocars, obturators, cannulas, endoscopic hand instruments such as graspers, forceps, scissors, etc., insufflators, endoscopes, surgical staplers, clip appliers, hernia repair instruments, and the like, are encompassed by this disclosure. In a particularly preferred embodiment, the principles of the present disclosure are applied to a disposable endoscope.

Figure 1:
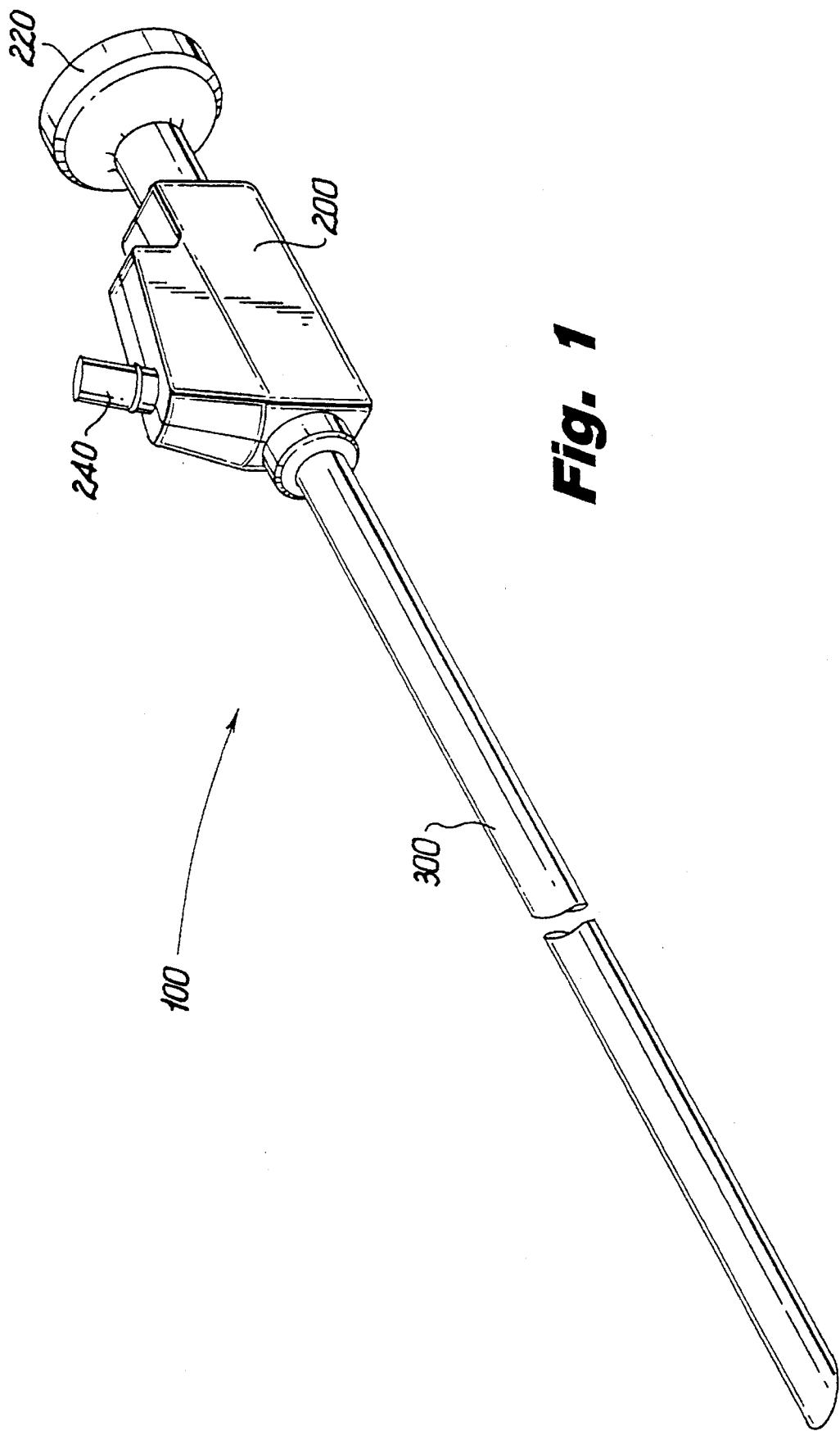
FIG. 1 is a perspective view of the disposable endoscope disclosed herein.

FIG. 1 illustrates, in perspective view, an endoscope 100 having a housing portion 200 and an endoscopic portion 300 extending distally from the housing portion 200. A preferred endoscope for use according to the present disclosure is described in U.S. Pat. No. 4,964,710 to Leiner, the disclosure of which is incorporated herein by reference. Although the endoscope depicted in the accompanying figures is a 0° (forward view) laparoscope, a wide variety of endoscope designs may benefit from the disabling mechanism described herein, e.g., a rigid endoscope, flexible endoscope, forward view endoscope and inclined angle-of-view endoscope. Housing portion 200 supports eyepiece assembly 220 which contains an eye lens assembly (not shown) for viewing the image of the object formed by the optical system of the endoscope. Light guide connector 240 connects a light guide, e.g., an optical fiber bundle (not shown), which provides illuminating light to the illumination system of endoscope 100.

Figure 2:
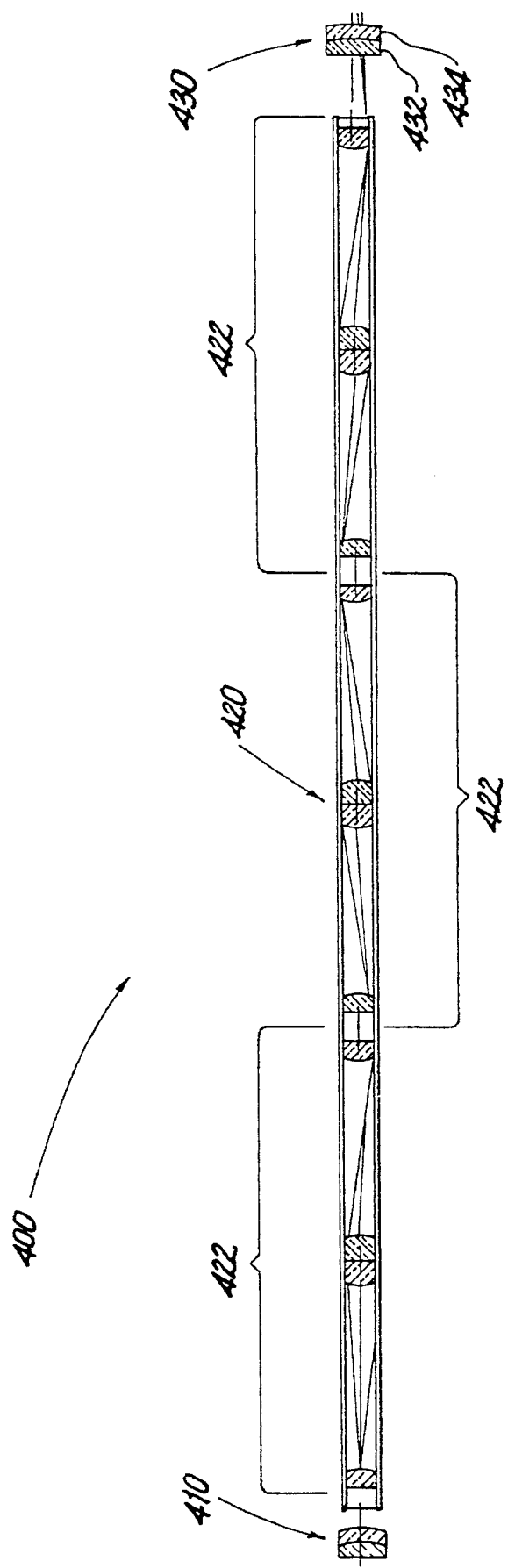
FIG. 2 is an optical schematic of an endoscopic optical system.

The optical system of endoscope 100 is depicted in FIG. 2. As shown in FIG. 2, optical system 400 includes three components: an objective lens assembly 410 for forming an inverted image of an object at an entrance image plane, a relay lens assembly 420 for transferring the image formed at the entrance image plane through the instrument to an exit image plane, and an eye lens assembly 430 for producing a magnified virtual image for the viewer. Each component of optical system 400, i.e., objective lens assembly 410, relay lens assembly 420 and eye lens assembly 430, defines an optical axis along which an image is transmitted. Optical system 400 is mounted in an endoscope tube in accordance with conventional methods. Thus, the objective lens and relay lens assemblies is typically supported by endoscopic portion 300 of endoscope 100.

Objective lens assembly 410 includes a plurality of curved lenses which are in optical alignment with each other and with the remaining components in the optical system. The lenses are geometrically configured to transfer an inverted image of an illuminated object from the object plane to an initial or entrance image plane prior to relay.

Relay lens assembly 420 includes at least one and preferably a plurality of relay lens modules 422 which can be arranged in end-to-end fashion along a common axis. Each module 422 can be identical with regard to the optical components contained therein and is capable of transferring an image from an image plane at the entrance side of the module to a successive image plane formed on the exit side. As shown in FIG. 2, relay lens assembly 420 includes three lens modules 422 aligned in end-to-end fashion along a common axis. In a preferred embodiment and as described in Leiner '710 incorporated hereinabove, the relay lens modules 422 preferably include plano glass cylinders and polymeric curved surface lenses.

Eye lens assembly 430 preferably includes a doublet lens having two lens elements 432 and 434 which are bonded to each other along adjacent end surfaces. Lens element 432 can be fabricated from a polymer such as an acrylic-based polymer and lens element 434 can be fabricated from second polymer such as a styrene-based polymer. Lens elements 432 and 434 can optionally be fabricated from other materials such as optical glass.

Figure 3:
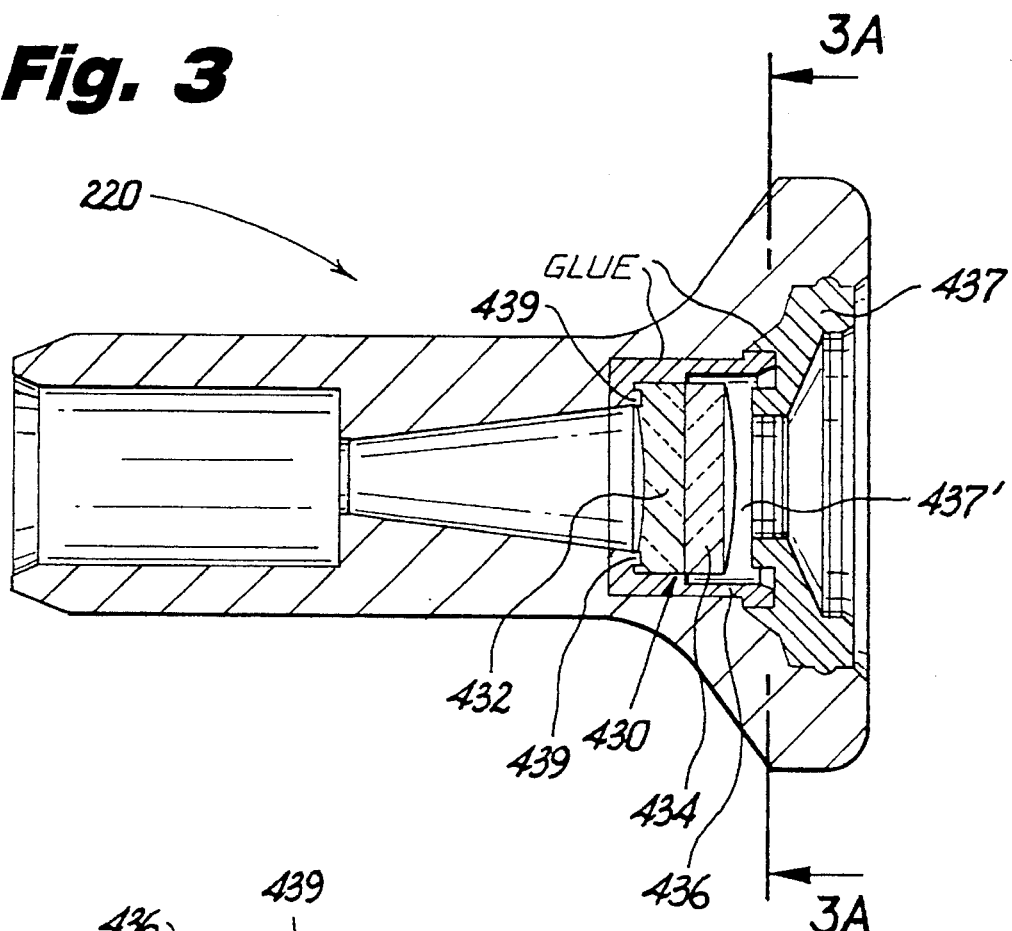
FIG. 3 is an enlarged cross-sectional view of the proximal end of the disposable endoscope disclosed herein.
Figure 3A:
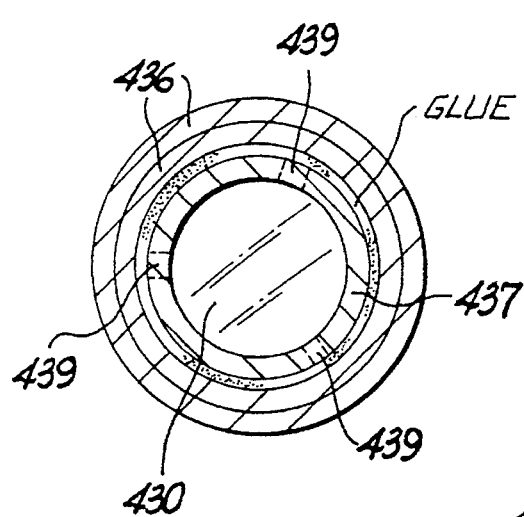
FIG. 3A is a cross-sectional view taken along line 3A—3A of FIG. 3.

Referring now to FIGS. 3 and 3A, eye lens assembly 430 is supported inside eyepiece assembly 220 by lens mounting element 436 which maintains eye lens assembly 430 in alignment with the optical axis of endoscope 100. The interior portion of eyepiece assembly 220 forms a cavity which is configured and dimensioned to receive lens mounting element 436 and eyepiece cup 437. Eyepiece cup 437 assists the viewer in focusing on eye lens assembly 430 where the magnified virtual image of the object is formed. An aperture 437' is formed by eyepiece cup 437 which allows ambient air to communicate with eye lens assembly 430 and lens mounting element 436. Lens mounting element 436 and eyepiece cup 437 can be secured to eyepiece assembly 220 by any suitable means, preferably with the use of an adhesive/glue as shown in FIG. 3.

Figure 4:
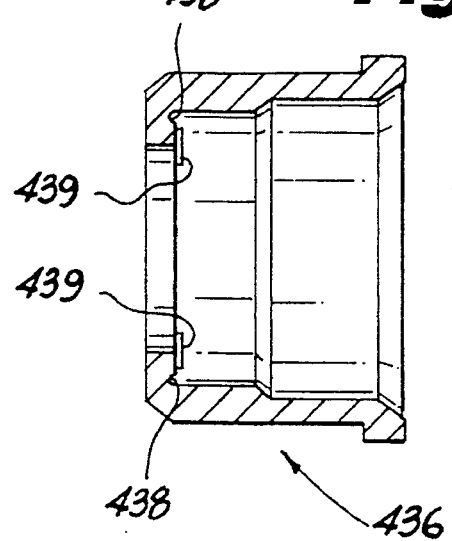
FIG. 4 is an enlarged cross-sectional view of the lens mounting element depicted in FIG. 3.

AS shown in FIG. 4, lens mounting element 436 is provided with detent 438 which receives the edges of concave lens element 432 as depicted in FIG. 3. Lens mounting element 436 is further optionally provided with buttons 439 which contact eye lens assembly 430 and assist in maintaining the eye lens assembly in optical alignment with the relay lens and objective lens assemblies of the instrument.

Lens mounting element 436 and/or buttons 439 are fabricated, e.g., molded, from a material such as a natural or synthetic polymer which is capable of deforming in the presence of a deforming agent such as water, organic solvent, heat, gas, light, or the like. When a water-soluble polymer is employed, the lens mounting element and/or buttons undergo a rapid deformation when exposed to water or organic solvents. This deformation process is gradual and may take from about 5 to about 30 minutes to fully deform, depending on the material utilized and the solvent employed. Specifically, when the instrument is exposed to suitable amounts of water or organic solvent as, e.g., when the instrument is subjected to steam treatment or washed with a cleaning fluid containing water or other organic solvent, the water or solvent is introduced through aperture 437' to the cavity inside eyepiece assembly 420 and contacts the lens mounting element and/or buttons fabricated from the water-soluble polymer As a result of this contact, the lens mounting element and/or buttons become rubbery in consistency, begin to flow and/or partially or completely dissolve within the water or solvent.

Any water-soluble polymer can be utilized in fabricating lens mounting element 436 and/or buttons 439 herein. Examples of water-soluble polymers include well known hydroxy-containing polymers such as the polyethylene oxides corresponding to the general formula $OCH_2CH_{2n}OH$, e.g., POLYOX® (Union Carbide), and polyvinyl alcohol, e.g., VINEX® (Air Products). Polyethylene oxide possessing an average molecular weight of from about 100,000 to about 8,000,000 and preferably from about 200,000 to about 400,000 can be advantageously employed herein and is generally preferred in carrying out the teachings of the present disclosure. Upon contact with suitable amounts of water, polyethylene oxide will partially or completely dissolve, become rubbery or begin to flow within a relatively short period of time, i.e., in about 5 to about 10 minutes, depending on the amount of water to which the polymer is exposed.

Once polyethylene oxide reacts with such moisture, lens mounting element 436 and/or buttons 439 fabricated therefrom will begin to deform. Deformation of the lens mounting element and/or buttons, in turn, deleteriously affects the orientation of eye lens assembly 430 which is held in alignment with the optical axis of endoscope 100 by lens mounting element 436 and, optionally, buttons 439. Consequently, the orientation of eye lens assembly 430 shifts relative to the optical axis of endoscope 100, thereby precluding or obstructing transmission of a clearly viewable image through the instrument.

In a related embodiment, at least one spring element such as ring-shaped spring washer 600 shown in FIG. 5 can be disposed between eyepiece assembly 220 and lens mounting element 436 in biasing abutment with lens mounting element 436 such that, upon deformation of the lens mounting element and/or buttons in the manner described herein, eye lens assembly 430 is forced out of its original alignment with the optical axis of endoscope 100. The action of spring washer 600 on lens mounting element 436 forces eye lens assembly 430 to deviate from its optical axis relative to the objective lens assembly and relay lens assembly of endoscope 100. Even relatively slight deviations from this axis will render the endoscope inoperable. While for purposes of illustration one spring washer is depicted, it should be understood that more than one spring element can be employed herein. Furthermore, the location of the spring element(s) can be changed so that the spring element(s) is (are) disposed directly between lens mounting element 436 and eye lens assembly 430.

Referring now to FIG. 6, in another embodiment herein, lens mounting element 436 shown in FIGS. 5 and 5A is provided with neck 437 and flange 435 for mounting the lens mounting element within eyepiece assembly 220 of endoscope 100. Neck 437 provides a point of weakness which tends to rapidly deform in the presence of a deforming agent. Thus, in accordance with this particular embodiment, deformation of the lens mounting element is accelerated.

While lens mounting element 436 is generally depicted as being cylindrical, it should be understood that the instant disclosure is not limited to a specific shape and/or configuration of the lens mounting element. Those skilled in the art will readily appreciate that the principles of the present disclosure can be implemented in a diverse number of ways. Thus, e.g., the other optical components of endoscope 100, i.e., the objective lens assembly and relay lens assembly, can be supported by mounting elements in a manner similar to that disclosed herein, provided a path of ingress for a deforming agent is available. Furthermore, it shall be understood that the disclosure is not limited to the use of an endoscope or a specific design of endoscope, but that the teachings of this disclosure can be applied to a variety of instruments, e.g., by fabricating a pin, link, spring or the like from a deformable material, and all endoscopes, e.g., rigid endoscopes, flexible endoscopes, forward view endoscopes, inclined angle-of-view endoscopes, and the like.

It is also contemplated that photodegradable polymers can be utilized to fabricate members of the instrument herein. Exposure of such polymers to electromagnetic radiation (light) will cause the polymers to deform. Deformation, as used in the present context, includes the photo-oxidative degradation of polymers involving both photochemical and thermal reactions. The most important effect of deformation on the physical properties of photodegradable polymers is the production of changes in molecular weight. Decreases in molecular weight as a result of chain scission will destroy mechanical strength. Polymers susceptible of undergoing photodegradation can be advantageously employed herein. Photodegradation of such polymers can also lead to discoloration of the polymer. Thus, it is contemplated that one or more lenses of the endoscope or clear, plastic shields disposed before said lenses can be coated with such a polymer. Upon exposure to photodegradation-initiating radiation, the polymer will convert from being a clear and transparent material to an opaque and foggy material, thereby obscuring the image formed by the optical system of the instrument.

In another embodiment of the present disclosure, an instrument can be provided with a decay mechanism which is initiated by exposing the instrument to an external light source or simply by maintaining the instrument in contact with atmospheric conditions for a critical period of time. Alternatively, an instrument can be fabricated with a material which reacts with ethylene oxide, a gas commonly employed in resterilization procedures, to cause destabilization of the material, and thus prevent light from being transmitted through the device. For example, a lens coating, e.g., an anti-reflection material, may be selected which is reactive with ethylene oxide to fog the lens, thereby impairing light transmission therethrough.

The endoscope disclosed herein can be provided with a plurality of apertures which access cavities inside the eyepiece assembly. Water and/or other fluids or gases can enter the apertures, e.g., during a washing procedure, and fill up the cavities inside the eyepiece assembly. These cavities can be disposed along the longitudinal axis of the device in front of or behind one or more lenses of the optical system thereof. The presence of water or gases inside these cavities will interfere with the transmission of a clear image by the optical system of the endoscope. The apertures can be opened by the removal of a label or tab covering such apertures sometime prior to washing the instrument.

It will be understood that various modifications may be made to the embodiments herein. For example, more than one optical component of the device can be supported by mounting elements which deform in the presence of deforming agent as disclosed herein. Therefore, the above disclosure should not be construed as limiting, but merely as exemplifications of preferred embodiments. Those skilled in the art will envision other modifications within the scope and spirit of the claims appended hereto.

What is claimed is:

1. An endoscope comprising at least one lens mounting element for supporting at least one lens assembly of the endoscope, said lens mounting element being fabricated with a readily degrading polymeric material deforming in a sterilization medium, thereby disabling the endoscope from further use.

2. The endoscope of claim 1 selected from the group consisting of a rigid endoscope, flexible endoscope, forward view endoscope and inclined angle-of-view endoscope.

3. The endoscope of claim 1 wherein the lens mounting element is fabricated from a polymer selected from the group consisting of a water-soluble polymer and photodegradable polymer.

4. The endoscope of claim 3 wherein the water-soluble polymer is selected from the group consisting of water-soluble hydroxy-containing polymers, polyethylene oxide and polyvinyl alcohol.

5. The endoscope of claim 1 wherein the deforming agent is selected from the group consisting of water, organic solvents, heat, light and gas.

6. The endoscope of claim 1 wherein the lens assembly is an eye lens assembly for forming a magnified virtual image of an object.

7. The endoscope of claim 1 wherein the lens mounting element includes a detent for receiving an edge of the lens assembly.

8. The endoscope of claim 1 wherein the lens mounting element includes a plurality of buttons.

9. The endoscope of claim 1 wherein the endoscope includes a housing portion and an endoscopic portion extending distally from the housing portion, the housing portion supporting an eyepiece assembly which contains an eye lens assembly for viewing the image of an object formed by the optical system of the endoscope.

10. The endoscope of claim 9 wherein the eyepiece assembly is configured and dimensioned to receive a lens mounting element for supporting the eye lens assembly within the eyepiece assembly.

11. The endoscope of claim 10 wherein at least one spring element is disposed between the eyepiece assembly and the lens mounting element.

12. The endoscope of claim 11 wherein the spring element constitutes a spring washer.

13. The endoscope of claim 11 wherein the lens mounting element is fabricated from a water-soluble polymer which is capable of deforming in the presence of a deforming agent.

14. The endoscope of claim 13 wherein the water-soluble polymer is polyethylene oxide and the deforming agent is selected from the group consisting of water and organic solvent.

15. An endoscope comprising an optical transmission system for conveying images to an eyepiece, at least a portion of the optical transmission system fabricated with a readily degrading polymeric material deforming in a sterilization medium, thereby disabling the endoscope from further use.

16. The endoscope of claim 15 wherein the material is selected from the group consisting of a water-soluble polymer and photodegradable polymer.

17. The endoscope of claim 16 wherein the water-soluble polymer is selected from the group consisting of water-soluble hydroxy-containing polymers, polyethylene oxide and polyvinyl alcohol.

18. The endoscope of claim 15 wherein the deforming agent is selected from the group consisting of water, organic solvents, heat, light and gas.

19. The endoscope of claim 15 wherein the material is polyethylene oxide and the deforming agent is selected from the group consisting of water and organic solvents.

20. The endoscope of claim 15 selected from the group consisting of a rigid endoscope, flexible endoscope, forward view endoscope and inclined angle-of-view endoscope.

* * * * *